United States Patent [19]

Haga et al.

[11] Patent Number: 5,344,648

[45] Date of Patent: Sep. 6, 1994

[54] CENTRAL NERVOUS SYSTEM ACTIVATOR AND TASTE ENHANCING FOOD ADDITIVE

[75] Inventors: Masanobu Haga; Keiji Wada, both of Hokkaido, Japan

[73] Assignee: Iatron Laboratories, Inc., Tokyo, Japan

[21] Appl. No.: 847,040

[22] PCT Filed: Jul. 19, 1991

[86] PCT No.: PCT/JP91/00965

§ 371 Date: Apr. 14, 1992

§ 102(e) Date: Apr. 14, 1992

[87] PCT Pub. No.: WO92/03143

PCT Pub. Date: Mar. 5, 1992

[30] Foreign Application Priority Data

Aug. 16, 1990 [JP] Japan .................................. 2-216346

[51] Int. Cl.$^5$ .................. A61K 35/78; A61K 31/35; A61K 31/34

[52] U.S. Cl. .................. 424/195.1; 514/453; 514/468

[58] Field of Search .................. 424/195.1; 514/453, 514/468

[56] References Cited

FOREIGN PATENT DOCUMENTS

| | | | |
|---|---|---|---|
| 57-20314 | 12/1982 | Japan | A61K 35/78 |
| 59-43928 | 10/1984 | Japan | A61K 35/78 |
| 2100650 | 4/1990 | Japan | A61K 35/78 |
| 2-83320 | 8/1990 | Japan | A61K 35/78 |

OTHER PUBLICATIONS

The Merck Index 9th ed. 1976 p. 718, II 5534.
Isolation of Limonin and Obacunone from Phellodendri Cortex . . . -Chloralose-Urethane, Chemical and Pharmaceutical Bulletin, vol. 38, No. 8, Aug. 1990-Keji Wada et al.

*Primary Examiner*—John W. Rollins
*Attorney, Agent, or Firm*—Burgess, Ryan and Wayne

[57] ABSTRACT

A central nervous system activator comprising a body or a dried product of a plant belonging to Rutaceae, or an extraction product selected from the group consisting of a lower alkane insoluble portion thereof, a lower fatty acid ester extract of the lower alkane insoluble portion, a lower fatty acid ester-halogenated lower alkane soluble portion of the lower fatty acid ester extract, a limonin fraction of the lower fatty acid ester-halogenated lower alkane soluble portion, and an obacunone fraction of the lower fatty acid ester-halogenated lower alkane soluble portion and a central nervous system activator comprising a limonoid. Further, a taste enhancing food additive comprising the above plant body or dried product or extraction product, or limonoid.

22 Claims, No Drawings

CENTRAL NERVOUS SYSTEM ACTIVATOR AND TASTE ENHANCING FOOD ADDITIVE

TECHNICAL FIELD

The present invention relates to a central nervous system activator and a taste enhancing food additive. More particularly, the present invention relates to a central nervous system activator and a taste enhancing food additive containing a processed product of a plant body of a plant belonging to the family Rutaceae or an extract thereof, or a limonoid.

BACKGROUND ART

Plants belonging to the family Rutaceae, for example, the bark (without pellicle) of the *Phellodendron amurense*, that is, Phellodendron Bark, or the powder thereof, that is, Phellodendron Bark Powder, have been used in the past as a stomachic. In the past, however, they have not been used for the purpose of activating the central nervous system. The present inventors found that, unexpectedly, the processed product of the plant body or the extract of a plant belonging to the family Rutaceae has an activity to activate the central nervous system.

Further, the present inventors found that the above-mentioned processed product of the plant body of the plant belonging to the family Rutaceae, in particular, the extract thereof, has a remarkable taste enhancing action.

The present invention is based on these discoveries.

SUMMARY OF THE INVENTION

Therefore, the present invention relates to a central nervous system activator comprising a body or a dried product of a plant belonging to Rutaceae, or an extraction product selected from the group consisting of a lower alkane insoluble portion thereof, a lower fatty acid ester extract of the lower alkane insoluble portion, a lower fatty acid ester/halogenated lower alkane soluble portion of the lower fatty acid ester extract, a limonin fraction of the lower fatty acid ester/halogenated lower alkane soluble portion, and an obacunone fraction of the lower fatty acid ester/halogenated lower alkane soluble portion.

Further, the present invention relates to a central nervous system activator comprising a limonoid.

Further, the present invention relates to a taste enhancing food additive by comprising a body or a dried product of a plant belonging to Rutaceae, or an extraction product selected from the group consisting of a lower alkane insoluble portion thereof, a lower fatty acid ester extract of the lower alkane insoluble portion, a lower fatty acid ester/halogenated lower alkane soluble portion of the lower fatty acid ester extract, a limonin fraction of the lower fatty acid ester/halogenated lower alkane soluble portion, and an obacunone fraction of the lower fatty acid ester/halogenated lower alkane soluble portion.

Further, the present invention relates to a taste enhancing food additive characterized by comprising a limonoid.

BEST MODE FOR CARRYING OUT THE INVENTION

The plants belonging to Rutaceae used in the present invention are plants belonging to Phellodendron (for example, *Phellodendron amurense Ruprecht*), plants belonging to Citrus (for example *Citrus limon BUBM. f., Citrus sinensis OSBECK., Citrus paradishi MACF.*), plants belonging to Evodia (for example, *Evodia rutaecarpa Hook. fil. et THOMSON*), and plants belonging to Dictamnus (for example, *Dictamnus albus L. subsp. dasycarpus KITAGAWA*).

The preferable plants are *Phellodendron amurense* and its variants (*P. amurense Rupr. var. japonicum (Maxim.) ohwi, P. amurense Pupr. var. sachalinense Fr. Schm., P. ammurense Rupr. var. lavallei (Dode) Sprague*, etc. ), *P. chinense Schneid* and its variants (*P. chinese Schneid. forma glabrinsculum (Schneid.) Hsiao, P. chinense Schneid. var. omeiense Huang, P. chinense Schneid. var. yunnanense Huang, P. chinense Schneid. var. falcatum Huang*, etc.), *P. wilsonii Hayata et Kanehira, Evodia rutaecarpa Hook. fil. et Thomson, Dictamnus albus L. subsp. dasycarpus KITAGAWA*, etc.

In the present invention, all or a part of the above plant bodies or a mixture thereof may be used as a starting material. The portions of the plant bodies used preferably are the stalk, leaves, fruit or rind, and the bark (in particular the plants of the Phellodendron), the roots (in particular the plants of the Dictamnus), or the seeds (in particular the plants of the Citrus).

The above plant bodies may be used in the present invention after crushing, grinding, pasting or juicing to obtain a processed product of the plant body, or further drying and pulverizing the above product to obtain a powdery processed product of the plant body.

The preferable processed product of the plant bodies are the Phellodendron Bark powder prepared by grinding, drying, and pulverizing the bark (without the pellicle) of the *Phellodendron amurense* (in which the later mentioned limotin and obacunone coexist in high contents and where it is considered the two ingredients mutually strengthen their actions) or concentrated juices, powdered juices or seeds. (high in limonin content) of the Citrus, such as *Citrus paradishi MACF., Citrus sinessisi OSBECK.* or the like.

In the present invention, it is possible to use an extraction product of the above-mentioned processed product of the plant body. The extraction products which may be used in the present invention are a lower alkane insoluble portion of the above processed product of the plant body, a lower fatty acid ester extract of the lower alkane insoluble portion, a lower fatty acid ester/halogenated lower alkane soluble portion of the lower fatty acid ester extract, a limonin fraction of the lower fatty acid ester/halogenated lower alkane soluble portion, or an obacunone fraction of the lower fatty acid ester/halogenated lower alkane soluble portion, or a mixture thereof.

The extraction process may be performed as follows, for example:

The processed product of the plant body is extracted under reflux by a lower alkane (for example, an alkane of 5 to 8 carbon atoms (preferably 5 to 7), for example, pentane, heptane, or hexane, in particular n-hexane). It is observed that the resulting extraction residue or dried product thereof (hereinafter referred to as the "alkane extraction residue") have activities to activate a central nervous system, and to enhance the taste of food.

The above-mentioned alkane extraction residue is extracted under reflux by a lower fatty acid ester (for example, a lower alkyl ester of an acetic, propionic, or burytic acid, preferably an acetic acid ester, in particular ethyl acetate). It is observed that the resulting extract or dried product thereof (hereinafter referred to as the "lower fatty acid ester extract") have activities to activate the central nervous system, and to enhance the taste of food.

Further, the lower fatty acid ester extract is treated by chromatography by a lower fatty acid ester (for example, the above-mentioned compounds, particularly acetic acid esters, particular ethyl acetate)/halogenated lower alkane (for example, a chloride compound of a lower alkane with 1 to 4 carbon atoms, in particular chloroform), optionally with gradually changing the ratio of a mixture of the above two mobile phases, to obtain a fraction containing limonin (hereinafter referred to as the "limonin fraction") or a fraction containing obacunone (hereinafter referred to as the "obacunone fraction"). It is observed that the resulting limonin fraction and the resulting obacunone fraction have activities to activate a central nervous system, and to enhance taste of food.

The above-mentioned processed products of the plant body or the extraction products thereof may be contained alone or in combination thereof in the central nervous system activator or the food additive according to the present invention.

Further, the central nervous system activator and the food additive of the present invention may comprise a limonoid. A limonoid is an oxidized derivative of the bitter tasting tetracyclic triterpens, which is contained in plants belonging to Rutaceae, Simaroubaceae, Meliaceae, etc. and the glycosides thereof. The preferable compounds belonging to the limonoids are limonin, obacunone, and the glycosides thereof. The limonoids may be separated and purified from the above extraction products, chemically synthesized, chemically or biologically derived, or biochemically synthesized.

The central nervous system activator of the present invention may be used in various forms for oral administration, for example, tablets, dispersions, granules, capsules, syrups, elixirs, or suspensions. These preparations may be prepared by a conventional manner.

In addition to the effective ingredient of the above-mentioned processed product of the plant body, the extraction product thereof, or limonoids (limonin, obacunone, etc.), the central nervous system activator of the present invention may contain, pharmaceutically acceptable carriers, for example, a general nontoxic carrier for oral administration, binder, lubricant, disintegrator, coloring agent, sweetener, flavor and/or preservative.

The central nervous system activator according to the present invention may be administrated orally to mammals (in particular human beings). The subjects to which the present activator is administrated are persons who are afflicted with drowsiness or malaise and require that the same be eliminated or reduced. The dose of the central nervous system activator of the present invention varies with the patient, the symptoms to be treated, and/or the form of the preparation. To obtain the desired effect, however, the dose should generally be 10 to 200 mg/kg per day, preferably 20 to 150 mg/kg for the above-mentioned processed product of the plant body or the extraction product thereof (as Phellodendron Bark Powder), and 0.05 to 10.0 mg/kg per day, preferably 0.1 to 5.0 mg/kg for the limonoids. In some cases, the dose can be increased. These amounts of administration may be given once a day or divided into several portions over a day.

By adding the food additive of the present invention to various foods, it is possible to enhance the taste. In the present specification, the term "taste enhancement" means imparting a refreshingness, vitality, cleanness, fineness, and/or bracingness to the inherent taste of the food.

The food where the addition of the food additive of the present invention particularly enhances the taste is not particularly limited. As examples of food where the addition of the food additive of the present invention is preferable, there may be mentioned confectionery, for example, sweets (such as candies, jellies), gums, beanpastes, baked confectioneries or molded confectioneries (for example, cookies and biscuits), steamed confectioneries; cacao or cacao products, for example, chocolates and cocoa; frozen confectioneries (such as ices and ice cream); beverages (such as fruit juice drinks, soft drinks (carbonated beverages), health drinks; tea, for example, green tea and black tea; coffee, or the like.

The food additive of the present invention may be used in the same manner as the conventional food additives, and thus, only needs to be mixed with the other components. The amount incorporated varies depending on the kind of the food, but in general, a single uptake contains an amount of 0.005 percent or more, preferably 0.01 percent or more of the present additive with respect to the amount of the limonoid.

The active component of the food additive of the present invention enhances the refreshingness of the taste and also has an activity to activate a central nervous system, so it is extremely preferable to add the food additive of the present invention to foods having stimulating applications (foods for dispelling drowsiness) (for example, refreshing drinks, foods for car drivers, health foods for the elderly), since it has a synergistic action.

EXAMPLES

The present invention will be concretely explained by examples hereinafter, but these examples are not intended to limit the scope of the invention in any way.

Example 1: Extraction Process

Phellodendron Bark Powder (Uchida Wakanyaku; 600 g) was inserted into an extraction tube of a Soxhlet extractor and subjected to an extraction treatment for 24 hours under reflux by 2000 ml of n-hexane. The n-hexane extraction residue (approximately 570 g) remaining in the extraction tube was removed (hereinafter referred to as the "n-hexane extraction residue A").

Then, 570 g of the n-hexane extraction residue A was inserted into an extraction tube of a Soxhlet extractor and subjected to an extraction treatment for 24 hours under reflux by 2000 ml of ethyl acetate. The ethyl acetate extraction residue (approximately 560 g) remaining in the extraction tube (hereinafter referred to as the "ethyl acetate extraction residue B") and the ethyl acetate extract (approximately 10 g) obtained in the extraction flask (hereinafter referred to as the "ethyl acetate extract C") were taken out. The same procedure was repeated five times to obtain a total of about 50 g of the ethyl acetate extract C.

The above-mentioned ethyl acetate extract C (50 g) was inserted into a glass column packed with 800 g of silica gel (Wacogel C-200; Wako Junyaku) and eluted by an ethyl acetate-chloroform mixture (10% by volume: 90% by volume).

The fractions No. 28 to No.35 (150 ml in each fraction) were colored an orange-red by Ehrlich's reagent on a thin layer chromatography, and exhibited absorption at 210 nm. The fractions No. 28 to No. 35 were purified by chloroform/ethanol to obtain approximately 5 g of colorless needle crystals. From the following physicochemical data, it was confirmed that the colorless needle crystals were limonin (hereinafter the above-mentioned colorless needle crystals will be referred to as the "limonin crystals D").

Melting point: 298° to 299° C.,

Specific rotatory power $[\alpha]_D = -107°$ (c=0.1; $CHCl_3$),

High resolution mass spectrum m/z: For $C_{26}H_{30}O_8$, Calculated: 470.1925; Found: 470.1933 (M+).

$^1$H-nuclear magnetic resonance spectrum (acetone-d6)δ: 1.13(s), 1.15(s), 1.21(s), 1.23(S), 4.08(S), 4.27(dd, J=2.6, 1.5 Hz), 4.63 (d, J=13.2 Hz), 4.98 (d, J=13.2 Hz), 5.53 (s), 6.51 (m), 7.57 (t, J=1.5 Hz), 7.63 (m).

Further, the fractions No. 7 to No. 15 were colored orange-red with Ehrlich's reagent on thin layer chromatography and showed absorption at 208 nm. The fractions No. 7 to No. 15 were purified by chloroform to obtain approximately 10 g of colorless columnar crystals. From the following physicochemical data, it was confirmed that the crystals were obacunone (hereinafter the above-mentioned colorless columnar crystals will be referred to as "obacunone crystals E").

Melting point: 228° to 229° C.,

Specific rotatory power $[\alpha]_D = -34°$ (c=0.1; acetone).

High resolution mass spectrum m/z: For $C_{26}H_{30}O_7$, Calculated: 454.1988; Found: 454.1990 (M+).

$^1$H-nuclear magnetic resonance spectrum (acetone-d6)δ: 1.13(s), 1.30(s), 1.42(s), 1.51(s), 1.53(s), 3.69(s), 5.51 (s), 5.86 (d, J=11.7 Hz), 6.52 (m), 6.80 (d, J=12.2 Hz), 7.57 (t, J=1.5 Hz), 7.64 (m).

Further, the fractions No. 1 to No. 6, the fractions No. 16 to No. 27, and the fractions No. 36 to No. 100 did not color orange-red by Ehrlich's reagent on thin layer chromatography. These fractions as a whole will be referred to as the "non-limonoid fraction F" hereinafter.

On the other hand, the fractions not eluted by the ethyl acetate-chloroform mixture will be referred to hereinafter as the "berberine fraction G".

Example 2: Pharmacological Effect

The various extraction components obtained in the above-mentioned Example 1 were administered to mice to investigate their pharmacological activities.

Test Procedure

Phellodendron Bark Powder (Uchida Wakanyaku), the n-hexane extraction residue A or ethyl acetate extraction residue B obtained in Example 1 was added into a powdered feed for mice [Oriental Yeast; Powdered Feed M; containing as main constituents soluble non-nitrogen substances (54.5 percent)], in an amount of 5 percent by weight and was mixed by a mortar. The ethyl acetate extract C, the limonin crystals D, the obacunone crystals E, the nonlimonin fraction F, and the berberine fraction G obtained in Example 1 were respectively added to the above-mentioned powdered feed for mice in an amount of 0.1 percent by weight and were mixed by a mortar. As a control, the powdered feed M was used. A fresh feed was given every day.

Further, the above-mentioned limonin crystals D and the obacunone crystals E were suspended in 0.25 percent aqueous solutions of sodium carboxymethylcellulose and administrated orally in amounts of 200 mg/kg once a day. As a control, 0.25 percent aqueous solution of sodium carboxymethylcellulose without the active component was used.

Three week-old ddY male mice were kept acclimated for one week before use as the test animals for the administration of the powdered feed. The difference in body weight affects the sleeping time, so the difference between groups was adjusted less than 10 percent and random extraction was carried out.

A wire net was placed at the bottom of the plastic cage at approximately 2 cm height, and the mice were placed on the net, so as to keep the mice from eating anything except for the feed. The feed and water were made freely available. Every two or three days, the body weights were measured and the state of uptake of the feed, the changes in body weight, or the like were compared with the control group.

For the oral administration test, mice having a body weight of 27 to 28 g were used after one week or more of regimen.

An α-chlorarose (50 mg/kg)-urethane (500 mg/kg) (anesthetic) physiological saline solution (0.1 ml/10 g body weight) was administered intraperitoneally into the mice. The time until the disappearance of the righting reflex (the reflex of the mouse immediately returning to the prone position when placed on its back; when anesthetized, this reflex disappears and the mouse is unable to rise up) and the changes in the sustained sleeping time were measured in each group. In this test, the time from the disappearance of the righting reflex until the recovery of the righting reflex was used as the sustained sleeping time. Further, the point of time when three righting reflexes were exhibited within one minute was considered the time when the righting reflex was recovered. The administrations to the groups were performed within three minutes. The body weights were measured before the administration of the anesthestic.

The results obtained were subjected to Smirnoff's rejection test, then the difference of the average values was examined by a t-test of Student. $P<0.05$ was considered significant.

Results (1) Change in Body Weight

There was no significant difference observed in the body weight between the control group and the groups wherein the powdered feed containing 5 % by weight of the Phellodendron Bark Powder, n-hexane extraction residue A, or ethyl acetate extraction residue B was administrated. Further, there was no significant difference observed in the body weight between the control group and the groups wherein the powdered feed containing 0.1% by weight of the ethyl acetate extract C, the limonin crystals D, the obacunone crystals E, the non-limonoid fraction F, or the berberine fraction G was administered. Further, there was no significant difference observed in the body weight between the control group and the groups wherein the sodium carboxymethylcellulose suspension of the limonin crystals D of the obacunone crystals E was administered.

(2) Sleeping Time

The measurement results are shown in the following

TABLE 1

| Administration period (days) | Group and N number | Body weight (g) | Sleeping time (min) | Sleep reducing rate (%) |
|---|---|---|---|---|
| 4 | Control (N = 0) | 23.6 ± 0.4 | 108.3 ± 9.1 | |
| 4 | Obacu (N = 12) | 23.0 ± 0.2 | 78.5 ± 7.2* | 28% |
| 7 | Control (N = 14) | 27.0 ± 0.5 | 94.7 ± 6.6 | |
| 7 | Obacu (N = 10) | 27.2 ± 0.3 | 58.8 ± 6.2** | 34% |
| 11 | Control (N = 10) | 30.9 ± 0.5 | 93.3 ± 11.6 | |
| 11 | Obacu (N = 9) | 29.9 ± 0.5 | 38.1 ± 3.1** | 59% |
| 11 | Control | 31.4 ± 0.4 | 63.7 ± 5.3 | |
| 11 | n-hexane extraction residue A (N = 9) | 29.9 ± 0.7 | (Note 1) | |
| 11 | Control (N = 9) | 32.9 ± 0.3 | 68.3 ± 11.1 | |
| 11 | Ethyl acetate extraction residue B (N = 9) | 29.9 ± 0.5 | 60.7 ± 4.6 | (Note 2) |
| 9 | Control (N = 10) | 29.0 ± 0.3 | 84.0 ± 6.0 | |
| 9 | Limonin crystals D (N = 11) | 30.6 ± 0.4 | 52.0 ± 5.3** | 38% |
| 9 | Obacunone crystals E (N = 10) | 28.6 ± 0.4 | 62.6 ± 5.2** | 25% |
| 9 | Non-limonoid fraction F (N = 10) | 31.1 ± 0.4 | 78.7 ± 9.5 | (Note 2) |
| 10 | Control (N = 7) | 29.7 ± 0.8 | 95.0 ± 11.4 | |
| 10 | Berberine fraction G (N = 7) | 30.1 ± 0.5 | 85.2 ± 6.7 | (Note 2) |
| 3 times (Note 3) | Control (N = 8) | 28.3 ± 0.7 | 96.1 ± 7.4 | |
| 3 times (Note 3) | Limonin crystals D (N = 8) | 28.6 ± 0.4 | 84.3 ± 9.9 | 12% |
| 3 times (Note 3) | Obacunone crystals E (N = 8) | 27.5 ± 0.5 | 53.0 ± 6.5** | 45% |

In Table 1, the sleep time reducing rate (S) is S = (1 − Sleeping time of administration group/Sleeping time of control group) × 100
All figures are average value ± standard error. The * and ** marks mean $P < 0.05$ and $P < 0.01$, respectively. N is the number of animals used.
Note 1: Disappearance of righting reflex not observed in five of nine mice.
Note 2: No significant difference.
Note 3: Three oral administrations of 200 mg/kg.

(3) Time Until Disappearance of righting Reflex

There was no significant difference observed in the time after the administration of the anesthetic to the disappearance of the righting reflex between the control group and the groups wherein the active components were administered. Further, in the dissection after the end of the experiment, in all cases, no particular abnormalities were observed in the organs compared with the control group.

Example 3: Preparation Process

One thousand tablets were manufactured from the following components.

| Component | Amount (g) |
|---|---|
| Phellodendron Bark Powder | 150 |
| Lactose (excipient) | 99.4 |
| Hydroxypropylcellulose (binder) | 0.6 |

-continued

| Component | Amount (g) |
|---|---|
| Magnesium stearate (lubricant) | 2.0 |

The above-mentioned components were thoroughly mixed and the mixture was sufficiently kneaded by an ordinary method, then was passed through the screen of an extrusion granulator to form granules, which were then sufficiently dried and pressed to form tablets. It is also possible to sufficiently mix the components and then direct press to form tablets.

Example 4: Citrus Juice Powder

Ten valencia oranges were divided and mixed, then placed in a centrifugal filtering machine to obtain the juice. To 9 volumes of the obtained juice was mixed 1 volume of an aqueous solution containing 30 percent carboxymethylcellulose and 20 percent sucrose as an excipient. The mixture was frozen by cooling to −60° C. and vacuum dried to obtain valencia orange juice powder. Further, juices of lemon and grapefruit were used and the same procedures followed to obtain lemon juice powder and grapefruit juice powder.

Pharmacological Effect

The freeze-dried juice powders obtained in the above Example 4 were administered to mice to investigate their physiological activity. The same procedure was repeated as in Example 2 except using powdered feed M including 5 percent by weight of the various juice powders. The results are shown in the following Table 2 (5 days administration) and Table 3 (11 days administration). In Tables 2 and 3, the sleep reducing rate (%) is the sleeping time as to the juice powder administrated groups in the case of the sleeping time of the control group as 100 percent. In the columns of the sleeping time, the figure in the 5% lemon row of Table 2 is $P<0.05$ and the figures in the 5% orange, 5% lemon, and 5% grapefruit rows of Table 3 are $P<0.01$.

TABLE 2

(5 Days Administration)

| Administered juice powder (N times) | Body weight (g) | Introduction time (min) | Sleeping time (min) | Sleep reducing rate (%) |
|---|---|---|---|---|
| Control (N = 8) | 28.13 ± 0.22 | 39.13 ± 5.72 | 86.88 ± 11.46 | 100.0 |
| 5% orange (N = 8) | 27.63 ± 0.38 | 39.25 ± 6.20 | 69.13 ± 6.83 | 79.6 |
| 5% lemon (N = 9) | 28.28 ± 1.64 | 32.67 ± 2.84 | 61.11 ± 5.89 | 70.3 |

TABLE 3

(11 Days Administration)

| Administered juice powder (N times) | Body weight (g) | Introduction time (min) | Sleeping time (min) | Sleep reducing rate (%) |
|---|---|---|---|---|
| Control (N = 10) | 38.45 ± 0.53 | 30.80 ± 2.02 | 114.89 ± 5.50 | 100.0 |
| 5% orange (N = 10) | 31.49 ± 0.77 | 38.40 ± 3.91 | 75.30 ± 6.97 | 65.5 |
| 5% lemon (N = 10) | 30.87 ± 0.87 | 39.60 ± 2.44 | 68.50 ± 10.85 | 59.6 |
| 5% grapefruit juice (N = 10) | 30.88 ± 0.74 | 32.44 ± 2.29 | 67.44 ± 10.17 | 58.7 |

Example 6: Beverage Composition

The three types of freeze-dried juice powder prepared in Example 4 and chemically synthesized limonin and obacunone were used to prepare five types of beverage compositions A to E and the control beverage composition having the following component ratios (unit: g):

| Composition | A | B | C | D | E | Control |
|---|---|---|---|---|---|---|
| Vitamin C | 0.2 | 0.2 | 0.2 | 0.2 | 0.2 | 0.2 |
| Vitamin $B_1$ | 0.001 | 0.001 | 0.001 | 0.001 | 0.001 | 0.001 |
| Vitamin $B_2$ | 0.001 | 0.001 | 0.001 | 0.001 | 0.001 | 0.001 |
| Vitamin $B_6$ | 0.002 | 0.002 | 0.002 | 0.002 | 0.002 | 0.002 |
| Vitamin E | 0.15 | 0.15 | 0.15 | 0.15 | 0.15 | 0.15 |
| Sugar | 45.0 | 45.0 | 45.0 | 45.0 | 45.0 | 45.0 |
| Fructose | 10.0 | 10.0 | 10.0 | 10.0 | 10.0 | 10.0 |
| Glucose | 9.0 | 9.0 | 9.0 | 9.0 | 9.0 | 9.0 |
| Citric acid | 0.5 | 0.5 | 0.5 | 0.5 | 0.5 | 0.5 |
| Calcium lactate pentahydrate | 0.1 | 0.1 | 0.1 | 0.1 | 0.1 | 0.1 |
| Magnesium chloride hexahydrate | 0.05 | 0.05 | 0.05 | 0.05 | 0.05 | 0.05 |
| Sodium citrate dihydrate | 0.5 | 0.5 | 0.5 | 0.5 | 0.5 | 0.5 |
| Sodium chloride | 0.7 | 0.7 | 0.7 | 0.7 | 0.7 | 0.7 |
| Calcium chloride | 0.4 | 0.4 | 0.4 | 0.4 | 0.4 | 0.4 |
| Orange juice powder | 10.0 | — | — | — | — | — |
| Lemon juice powder | — | 10.0 | — | — | — | — |
| Grapefruit juice powder | — | — | 10.0 | — | — | — |
| Obacunone | — | — | — | 0.5 | — | — |
| Limonin | — | — | — | — | 0.5 | — |
| Flavor | 1.0 | 1.0 | 1.0 | 1.0 | 1.0 | 1.0 |

Purified water to a total of 1 liter

Panel Test

The resulting beverages were used for a functional test by 20 adult male panelers. The evaluation was carried out by drinking 140 ml of a control beverage, and then immediately thereafter drinking 140 ml of the test beverage to judge if the test beverage did not have a worse taste in drinking in comparison with the control beverage (pleasantness of drinking) and if the test beverage was more refreshing than the control beverage (refreshingness). The following table shows the number of the panelers who evaluated the test beverages as being more pleasant to drink and refreshing:

| Beverage | Pleasantness of drinking | Refreshingness |
|---|---|---|
| A | 19 | 12 |
| B | 17 | 11 |
| C | 19 | 11 |
| D | 17 | 12 |
| E | 17 | 12 |

Example 6: Chewing Gum

The three types of freeze-dried juice powder prepared in Example 4 and chemically synthesized limonin and obacunone were used to prepare five types of chewing gums A to E and the control chewing gum of the following component ratios (unit: g):

| Component | A | B | C | D | E | Control |
|---|---|---|---|---|---|---|
| Gum base | 25 | 25 | 25 | 25 | 25 | 25 |
| Sugar | 60 | 60 | 60 | 60 | 60 | 60 |
| Thick malt syrup | 10 | 10 | 10 | 10 | 10 | 10 |
| Flavor | 1 | 1 | 1 | 1 | 1 | 1 |
| Orange juice powder | 4 | — | — | — | — | — |
| Lemon juice powder | — | 4 | — | — | — | — |
| Grapefruit juice powder | — | — | 4 | — | — | — |
| Limonin | — | — | — | 0.2 | — | — |
| Obacunone | — | — | — | — | 0.2 | — |

Panel Test

The resulting chewing gums were used for a functional test by 20 adult male panelers. The evaluation was carried out by chewing 5 g of a control chewing gum, and then immediately chewing 5 g of the test chewing gum to judge if the test chewing gum did not have a worse taste in chewing in comparison with the control gum (pleasantness of chewing) and if the test chewing gum was more refreshing than the control chewing gum (refreshingness). The following table shows the number of the panelers who evaluated the gum as being pleasantness to chew and refreshing:

| Gum | Pleasantness of chewing | Refreshingness |
|---|---|---|
| A | 14 | 10 |
| B | 13 | 10 |
| C | 13 | 10 |
| D | 12 | 11 |
| E | 13 | 10 |

Example 7: Candies

The orange freeze-dried juice powder prepared in Example 4 and chemically synthesized limonin and obacunone were used to prepared three types of candies of the following component ratios (unit: g, each piece about 5 g), which were used for panel tests as in Examples 5 and 6, whereupon substantially the same results were obtained as in Examples 5 and 6.

| Component | A | B | C |
|---|---|---|---|
| Sugar | 80 | 80 | 80 |
| Thick malt syrup | 20 | 20 | 20 |
| Flavor | 0.1 | 0.1 | 0.1 |
| Orange juice powder | 4.0 | — | — |
| Limonin | — | 0.2 | — |
| Obacunone | — | — | 0.2 |

Example 8: Cookies

The grapefruit freeze-dried juice powder prepared in Example 4 and chemically synthesized limonin and obacunone were used to prepared three types of cookies of the following component ratios (unit: g, 100 pieces worth), which were used for panel tests as in Examples 5 and 6, whereupon substantially the same results were obtained as in Examples 5 and 6.

| Component | A | B | C |
|---|---|---|---|
| Wheat flour | 450 | 450 | 450 |
| Sugar | 250 | 250 | 250 |

-continued

| Component | A | B | C |
|---|---|---|---|
| Butter | 150 | 150 | 150 |
| Egg | 100 | 100 | 100 |
| Flavor | 0.1 | 0.1 | 0.1 |
| Grapefruit juice powder | 10.0 | — | — |
| Limonin | — | 0.5 | — |
| Obacunone | — | — | 0.5 |

INDUSTRIAL APPLICABILITY

The central nervous system activator of the present invention contains as an active component the processed product of the plant body or the extraction product of the plant of Rutaceae, or the limonoid generally contained in plants of Rutaceae, and can be incorporated into food and taken up naturally.

Further, the processed product of the plant body or the extraction product of the plant of Rutaceae, or the limonoid generally contained in the plants of Rutaceae can enhance the refreshingness of the taste, when added to food.

We claim:

1. A method for activating the central nervous system of a warm blooded animal comprising administering to said warm blooded animal a central nervous system activating effective amount of body parts of a plant belonging to Rutaceae, or an extraction product selected from the group consisting of a lower alkane insoluble portion thereof, a lower fatty acid ester extract of the lower alkane soluble portion of the lower fatty acid ester extract, a limonin fraction of the lower fatty acid ester-halogenated lower alkane soluble portion, and an obacunone fraction of the lower fatty acid ester-halogenated lower alkane soluble portion.

2. A method according to claim 1, wherein said processed product of the plant body or the extraction product is administered orally in an amount of 10 to 200 mg/kg per day.

3. A method according to claim 1, wherein the plant belonging to Rutaceae is a plant belonging to Phellodendron.

4. A method according to claim 1, wherein the plant belonging to Rutaceae is a plant belonging to Citrus.

5. A method according to claim 1, wherein the plant belonging to Rutaceae is a plant belonging to Evodia.

6. A method according to claim 1, wherein the plant belonging to Rutaceae is a plant belonging to Dictamnus.

7. A method according to claim 1, wherein the extraction product is the lower alkane insoluble portion.

8. A method according to claim 1, wherein the extraction product is the lower fatty acid ester extract of the lower alkane insoluble portion.

9. A method according to claim 1, wherein the extraction product is the lower fatty acid ester/-halogenated lower alkane soluble portion of the lower fatty acid ester extract.

10. A method according to claim 1, wherein the extraction product is the limonin fraction of the lower fatty acid ester/halogenated lower alkane soluble portion.

11. A method according to claim 1, wherein the extraction product is the obacunone fraction of the lower fatty acid ester-halogenated lower alkane soluble portion.

12. A method according to claim 1 wherein the activating of the central nervous system is to arouse the warm blood animal.

13. A method according to claim 1, wherein the activating of the central nervous system is to eliminate or reduce drowsiness or malaise.

14. A method according to claim 1, wherein the activating of the central nervous system is to shorten a sleeping time.

15. A method for enhancing the taste of food comprising adding to said food, body parts of a plant belonging to Rutaceae, or a processed product thereof.

16. A method according to claim 15, wherein the processed product is an extraction product selected from the group consisting of a lower alkane insoluble portion thereof, a lower fatty acid ester extract of the lower alkane soluble portion of the lower fatty acid ester extract, a limonin fraction of the lower fatty acid ester-halogenated lower alkane soluble portion, and an obacunone fraction of the lower fatty acid ester-halogenated lower alkane soluble portion.

17. A method according to claim 15 for enhancing taste of food comprising adding to said food limonoid.

18. A method for activating the central nervous system of a warm blooded animal in need of such treatment, which comprises administering to said animal a central nervous system activating effective amount of a limonoid.

19. The method of claim 18 wherein the limonoid is administered orally in an amount of 0.05 to 10.0 mg/kg per day.

20. The method of claim 18 wherein the limonoid is limonin.

21. A method for activating the central nervous system in a warm blooded animal in need of such treatment, which comprises administering to said animal a central nervous system activating effective amount of obacunone.

22. A central nervous system activator comprising an extraction product of a plant belonging to Rutaceae selected from the group consisting of a lower alkane insoluble portion thereof, a lower fatty acid ester extract of the lower alkane insoluble portion, and a lower fatty acid ester-halogenated lower alkane soluble portion of the lower fatty acid ester extract and a pharmaceutically acceptable carrier.

* * * * *